US006475496B1

(12) United States Patent
Arminas et al.

(10) Patent No.: US 6,475,496 B1
(45) Date of Patent: Nov. 5, 2002

(54) GELLED COSMETIC REMOVER COMPOSITION

(75) Inventors: Scott Arnold Arminas, Jackson, NJ (US); Joseph Frank Calello, Bridgewater, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/640,266

(22) Filed: Aug. 17, 2000

(51) Int. Cl.$^7$ .......................... A61K 7/047; A61K 7/00; A61K 31/045; A61K 7/04; A01N 25/04
(52) U.S. Cl. ...................... 424/401; 424/486; 424/501; 424/61; 514/724; 514/770; 514/944; 514/949; 510/118
(58) Field of Search ................................. 424/401, 486, 424/501, 61; 510/118; 514/724, 770, 944, 949

(56) References Cited

U.S. PATENT DOCUMENTS

| 4,087,555 A | 5/1978 | Barnett ........................ 424/357 |
| 4,129,645 A | 12/1978 | Barnett ........................ 424/60 |
| 4,350,605 A | 9/1982 | Hughett ........................ 252/305 |
| 4,370,174 A | 1/1983 | Braithwaite .................... 137/7 |
| 4,381,248 A | 4/1983 | Lazar ........................... 252/118 |
| 4,446,051 A | 5/1984 | Berthod ........................ 252/309 |
| 4,626,428 A | 12/1986 | Weisberg ...................... 424/61 |
| 4,637,933 A | 1/1987 | Zabatto ........................ 424/131 |
| 4,704,234 A | 11/1987 | Petersen ....................... 252/542 |
| 4,830,843 A | 5/1989 | Usui ........................... 423/331 |
| 4,913,898 A | 4/1990 | Altobelli ....................... 424/70 |
| 4,927,556 A | 5/1990 | Pokorny ....................... 252/173 |
| 5,098,591 A | 3/1992 | Stevens ........................ 252/162 |
| 5,167,853 A | 12/1992 | Stevens ........................ 252/162 |
| 5,243,503 A | 9/1993 | Minick ......................... 132/38 |
| 5,486,499 A | 1/1996 | Davies ......................... 502/81 |
| 5,543,085 A * | 8/1996 | Miner et al. ................. 510/118 |
| 5,641,890 A * | 6/1997 | Wesley et al. ................. 44/266 |

FOREIGN PATENT DOCUMENTS

JP      10045565 A2 *    2/1998       A61K/7/50

OTHER PUBLICATIONS

Yamazaki et al., Skin Cleanser Composition Containing Non–Ionic Surfactants and Water–Swellable Clay Minerals, Feb. 17, 1998, JP 10045565 A2, abstract.*
Yamazaki et al., Detergent Composition, Feb. 17, 1998, JP 10045565 A2, abstract.*
Yamazaki et al., Detergent composition used as a facial cleaner for make–up removal—comprises non–ionic surfactant(s) and water swellable clay mineral(s), one or more mono–hydric, di–hydric or poly–hydric, Feb. 17, 1998, JP 10045565 A2, abstract.*
Laporte Industries, LTD., Aug. 16, 2000, Laponite web site, pp. 1–23.*
Laporte, Laponite Products, Laponite Technical Brief, Preparing Laponite Gels in Water, Jan. 1, 1987.

* cited by examiner

Primary Examiner—Frederick Krass
Assistant Examiner—Clinton Ostrup
(74) Attorney, Agent, or Firm—Julie Blackburn

(57) ABSTRACT

An organic solvent based cosmetic remover composition gelled to a viscosity of 25 to 500,000 centipoise with a synthetic metal silicate gelling agent.

20 Claims, No Drawings

GELLED COSMETIC REMOVER COMPOSITION

TECHNICAL FIELD

The invention is in the field of cosmetic compositions used for removing polymeric films from keratinous surfaces.

BACKGROUND OF THE INVENTION

Most often, it is desirable that cosmetic compositions applied to keratinous surfaces form some type of film on the keratinous surface. The tenacity and durability of the film formed depends on the type of cosmetic that is applied. For example, in nail enamel compositions, it is most desirable that the nail enamel film permanently adhere to the nail and be durable enough to withstand normal wear for at least several days. On the other hand, cosmetics such as eye or face makeup are generally worn for only one day and removed at the end of the day prior to retiring. Most cosmetic compositions that form a film on a keratinous surface contain at least one type of synthetic or natural film forming polymer which facilitates adhesion to the keratinous surface, and provides durability of the film while on the surface.

Cosmetic films can be removed from keratinous surfaces in a variety of ways. Certain cosmetics such as foundations, eye makeup, and the like can simply be washed off with water, or removed with commercially available makeup removers. Removal of cosmetic films formed by certain transfer resistant lipsticks or nail enamel may necessitate remover compositions containing certain types of solvents that are strong enough to dissolve the film formed by the cosmetic composition.

There are a number of problems with current commercial cosmetic remover compositions. The first is that most of such compositions are in the liquid form. Thus, if applied to the keratinous surface too generously, the remover may drip onto neighboring areas of the body, or onto clothing or household objects. This is not only uncomfortable for the user, but it may cause staining of clothing or objects as well. The second problem with commercially available removers is that they may be drying to the keratinous surface due to the presence of the inorganic solvents. The organic solvents, in turn, are necessary to effect removal of the cosmetic composition from the keratinous surface.

In order to eliminate the problem with dripping, various types of cosmetic remover compositions have been prepared in the gel form. These removers have a higher viscosity than the liquid removers, and will not readily drip off of the keratinous surface to which they are applied, or migrate from the area to which they are applied to other neighboring areas. Gelled remover compositions are not difficult to make, and a number of them are still commercially available. However, the problem still remains that these remover compositions do not exhibit any improvements in conditioning or moisturizing the keratinous surface. Rather, they tend to be the same drying formulas as the liquid formulas.

There is a need for cosmetic remover compositions which are gelled to a viscosity that permit easy application and minimizes dripping or migration, and at the same time provides superior moisturization and conditioning to the keratinous surface.

It is an object of the invention to provide cosmetic remover compositions in the gel form.

It is a further object of the invention to provide cosmetic remover compositions in the gel form and which also provide moisturizing and conditioning benefit to the keratinous surface.

It is a further object of the invention to provide a cosmetic remover composition gelled with a synthetic metal silicate gelling agent.

SUMMARY OF THE INVENTION

The invention is directed to an organic solvent based cosmetic remover composition gelled to a viscosity of 25 to 500,000 centipoise with a synthetic metal silicate gelling agent.

The invention is also directed to a method for gelling an organic solvent based cosmetic remover composition to a viscosity of 25 to 500,000 centipoise with a synthetic metal silicate gelling agent.

DETAILED DESCRIPTION

All percentages mentioned herein are percentages by weight unless otherwise indicated.

The term "cosmetic remover composition" means a composition that, when applied to a keratinous surface having a cosmetic film thereon, is capable of removing the cosmetic film from the keratinous surface in reasonable period of time. A reasonable period of time is the amount of time consumers traditionally allot for such makeup removal, and can range from fractions of a second up to one minute, possibly longer. The cosmetic remover composition may be applied by brushing onto the keratinous surface with a brush impregnated with the remover composition, or by impregnating an applicator with the remover composition and rubbing the keratinous surface having the cosmetic film thereon, or by dipping the keratinous surface into a remover composition one or more time to remove the film. An example of the latter type of removal is a container having the remover composition therein, in the form of a hard gel that is capable of exerting sufficient pressure on the keratinous surface dipped therein such that the film will be removed.

The term "organic solvent based" means that the cosmetic remover composition contains sufficient organic solvent to efficaciously remove the cosmetic film from the keratinous surface. The organic solvent based cosmetic remover composition may by anhydrous, or aqueous based.

The cosmetic remover composition remover composition comprises at least one organic solvent capable of removing the cosmetic film on the keratinous surface, and at least one synthetic metal silicate gelling agent as further described herein.

The Organic Solvent

The cosmetic remover composition is organic solvent based. Of the organic solvents used in the composition, at least one organic solvent should be capable of removing, either by itself, or when combined with other organic solvents, the cosmetic film on the keratinous surface. Suitable organic solvents are non-aqueous, and include hydrocarbons, organic alcohols, ketones, esters of organic alcohols, glycols, ethers, and the like. Preferably, one or more of the organic solvents are volatile, e.g. have a vapor pressure of at least 2 mm. of mercury at 20° C. The claimed composition comprises 0.5 to 95%, preferably 1–85%, more preferably 15–60% by weight of the total composition of one or more organic solvents.

Organic alcohols are suitable for use as the organic solvent in the claimed compositions, and include aliphatic or aromatic mono-, di- or trifunctional alcohols. Preferably, the organic alcohols are $C_{1-8}$ aliphatic mono- or difunctional alcohols, or C1–8 alkoxy alkyl alcohlols, or aromatic alcohols, such as ethanol, isopropanol, butanol, butylene glycol, ethylene glycol, propylene glycol, benzyl alcohol, butoxyethanol, butoxypropanol, butoxyisopropanol, and the like.

Suitable ketones are aliphatic or aromatic ketones having the general formula R—CO—R wherein each R is independently a $C_{1-8}$ alkyl, or benzyl, or R—CO—R forms a lactone. Examples of such ketones include acetone, propanone butyrolactone, methyl ethyl ketone, diacetone alcohol, and the like.

Suitable esters of organic alcohols include C1–8 aliphatic or aromatic acids, reacted with C1–8 aliphatic mono-, or difunctional, or aromatic, alcohols. Examples of such alcohols include butyl acetate, ethyl acetate, benzyl acetate, benzyl benzoate, benzyl glycol, butylene glycol propionate, butyl octanol, dibutyl adipate, dibutyl oxalate, dibutyl phthalate, dibutyl sebacate, isobutyl acetate, isoamyl acetate, and the like.

Suitable ethers include those of the formula R—O—R wherein each R is independently a C1–10 alkyl, a C1–10 alkoxy alkyl, or benzyl. Suitable examples of such ethers include methyl ether, ethyl ether, propyl ether, benzyl glycol, butoxydiglycol, and the like.

Also suitable are various straight or branched chain paraffinic hydrocarbons having 5 to 20 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

Preferred organic solvents depend on the type of remover composition that is being formulated. In nail enamel remover compositions, the preferred organic solvents are esters or ketones, either alone or in combination with C1–4 aliphatic or aromatic alcohols. Preferred organic solvents for use in compositions for removal of makeup from the eyes and face are paraffinic hydrocarbons.

The Metal Silicate Gelling Agent

The claimed compositions contain a synthetic metal silicate gelling agent in an amount sufficient to gel the remover composition to a viscosity ranging from 25 to 500,000 centipoise at room temperature (25° C.). The term "synthetic" means that the gelling agent is synthesized from simple silicates and salts in the presence of mineralizing agents, in contrast to natural metal silicates such as bentonite or hectorite which are obtained from clay and tend to be heavily contaminated with other minerals such as dolomite or quartz, which are not easily removed. The term "gelling agent" means that the synthetic metal silicate is capable of gelling a polar material into a gel or sol state. A gel is a high viscosity colloidal dispersion and a sol is a low viscosity colloidal dispersion. Preferred metal silicates for use in the claimed composition, at a concentration of 2% w/w in water, provide a Bingham Yield Value ranging from 25 to 250 dynes/cm². The term "Bingham Yield Value" is defined as the shear stress which has to be exceeded before the rate of shear shows a linear relationship to the shear stress. The Bingham Yield Value is generally determined by obtaining a flow curve relating the shear stress to the rate of shear, and then extrapolating the straight line section of the curve to the shear stress axis, with the intercept being the Bingham Yield Value. The metal silicate gelling agent is preferably an alkali metal silicate or alkaline earth metal silicate gelling agent. Suitable alkali metals or alkaline earth metals include sodium, potassium, magnesium, lithium, and the like. The most desirable synthetic metal silicates for use in the claimed compositions will provide remover compositions where the undisturbed viscosity of the remover composition is greater than the disturbed viscosity. In other words, when these compositions are subjected to shear stress the viscosity will decrease temporarily, and if no further shear stress is applied, the gel will reform and the composition will return to its original viscosity. Preferably the undisturbed viscosity at room temperature (25° C.) is 10 to 90% greater than the disturbed viscosity. For example, the disturbed viscosity of one embodiment of the claimed composition may be 20,000 centipoise and the undisturbed viscosity 50,000 centipoise. In this example, the undisturbed viscosity of the composition is 71% greater than the disturbed viscosity.

The synthetic metal silicates may be made in a variety of ways well known in the art. For example, Granquist and Pollack, in Clays and Clay Minerals, on pages 150–169, teach the manufacture of synthetic metal silicates by combining pre-washed gels of magnesium hydroxide and silica and redispersing in water to form a suspension. Then lithium hydroxide, lithium fluoride, or sodium hydroxide are added to the suspension, which is then treated hydrothermally by refluxing with stirring until a product having a crystal structure similar to hectorite is formed.

Another synthetic metal silicate suitable for use in the claimed composition may be synthesized as described in U.S. Pat. No. 3,586,478, which is hereby incorporated by reference. The '478 patent teaches the formation of synthetic metal silicates by forming an aqueous slurry of a water soluble magnesium salt, sodium silicate, sodium carbonate and/or sodium hydroxide, and a source of lithium or fluoride ions which may be lithium fluoride or a lithium compound in conjunction with hydrofluoric acid, fluosilicic acid, sodium silico fluoride, or sodium fluoride. The aqueous slurry is formed by co-precipitation by combining the magnesium salt, the acid sodium silicate, and the sodium carbonate or hydroxide with heating and agitation in an aqueous medium which contains the source of fluoride ions. Synthetic metal silicates prepared in this manner have the general formula:

$(Si_8Mg_{6-x}Li_x \cdot O_{20} \cdot (OH)_{4-y}F_y) \cdot x(-) \cdot x/nM^{a(-)}$ wherein:

x is between 0 and 6 y is 1 to 4; and

M is a cation which is preferably sodium or potassium.

Also suitable are synthetic metal silicates made as described in British Patent No. 1,213,122. These metal silicates are made by combining a water soluble magnesium salt with an aqueous alkaline solution of one or more sodium compounds in the presence of the dissolved silicon material, while maintaining the pH from 8 to 12.5, and thereafter exposing the mixture to high temperature and pressure. The resulting solid and liquid phases are then separated to obtain the synthetic metal silicate. Such metal silicates preferably have the general formula:

$$[Si_aMg_aLi_bH_{4+c}O_{24}]^{(12-2a-b-c)-} \cdot M(12-2a-b-c)^+$$

wherein:

M is sodium, lithium, or an organic cation the value of a, b, and c are such that a<6; b>0; c>0;

and b+c<2; +/−(a+b+c−6)<2 or a<6; b=0; +/−c<2.

Particularly preferred for use in the claimed compositions are synthetic metal silicates as described in British Patent No. 1,432,770. These metal silicates are made by forming an aqueous suspension of magnesium carbonate, and forming a silica precipiate in the aqueous suspension. The mixture is maintained in the wet state and subjected to a hydrothermal treatment by heating in an aqueous medium in the presence of the remaining constituents of the magnesium silicate until crystal growth occurs. The resulting crystalline products are then separated. The resulting synthetic metal silicate has the following general formula:

$$[Si_8(Mg_aLi_bH_c)O_{20}(OH)_{4-y}F_y]^{z-} \cdot zM+$$

wherein:

a is 4.95 to 5.7 b is from 0 to 1.05 c is from 0 to <2 a+b+c is from >4 to<8 y is from 0 to <4 z=12−2a-b-c

M is Na$^+$ or Li

Particularly preferred are synthetic metal silicates sold by LaPorte Industries Limited under the tradename Laponite. These synthetic metal silicates are made by combining salts of sodium, magnesium, and lithium with sodium silicate at controlled rates and temperatures. The amorphous precipitate produced is then partially crystallized at elevated temperatures which, after washing and drying, provides a fine white powder. Suitable Laponites include XLG and XLS, which are free flowing white powders, preferably free of fluoride, having the name of hydrous sodium lithium magnesium silicate.

The claimed composition may contain from about 0.01–20%, preferably 0.1–15%, more preferably 0.5–10% by weight of the total composition of the synthetic metal silicate gelling agent.

Water

Preferred remover compositions comprise water. Suggested amounts of water range from 0.5–95%, preferably 1–85%, more preferably 5–75% by weight of the total composition.

Other Ingredients

It may also be desirable to include other ingredients in the remover compositions including surfactants, emollients, stabilizing agents, and the like.

Surfactants

Suitable surfactants include nonionic, anionic, amphoteric, or zwitterionic surfactants. The surfactant, if present, may range from 0.01–20%, preferably 0.05–15%, more preferably 0.1–15% by weight of the total composition. Preferred are nonionic surfactants, including those produced by the condensation of alkylene oxide groups with a hydrophobic compound. Examples of nonionic surfactants are:

(a) Long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(b) Polysorbates, such as sucrose esters of fatty acids. Examples of such materials include sucrose cocoate, sucrose behenate, and so on.

(c) Polyethylene oxide condensates of alkyl phenols, for example the condensation products of alkyl phenols having an alkyl group of 6 to 20 carbon atoms with ethylene oxide being present in amounts of about 10 to 60 moles of ethylene oxide per mole of alkyl phenol.

(d) Condensation products of ethylene oxide with the reaction product of propylene oxide and ethylene diamine.

(e) Condensation products of aliphatic alcohols having 8 to 18 carbon atoms with ethylene oxide, for example a coconut alcohol/ethylene oxide condensate having 10 to 30 moles of ethylene oxide per mole of coconut alcohol, the coconut alcohol fraction having 10 to 14 carbon atoms. Particularly preferred are polyethylene glycol ethers of methyl glucose, also referred to as methyl gluceth.

(f) Long chain tertiary amine oxides such as those corresponding to the general formula:

$$R_1R_2R_3NO$$

wherein $R_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and $R_2$ and $R_3$ are each alkyl or monohydroxyalkyl groups containing from about 1 to about 3 carbon atoms.

(g) Long chain tertiary phosphine oxides corresponding to the general formula:

$$RR_1R_2PO$$

wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

(h) Polyethylene glycol (PEG) glyceryl fatty esters, having the formula $$RC(O)OCH_2CH(OH)CH_2(OCH_2CH_2)_nOH$$

wherein n is 5–200 and RC(O)—is a hydrocarbylcarbonyl group wherein R is preferably an aliphatic radical having 7 to 19 carbon atoms.

(i) $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

(j) Alkyl polysaccharides having a hydrophobic group of 6 to 30, preferably 10, carbon atoms and a polysaccharide group such as glucose, galactose, etc. Suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on.

Secondary Gelling Agent

It may also be desirable to incorporate one or more secondary gelling agents in the composition. Suitable gelling agents may be present at 0.001–20%, preferably 0.005–15%, more preferably 0.01–10% by weight of the total composition.

Suitable gelling agents include acrylic polymers, carboxylated salts, propylene carbonate, and so on.

The term "carboxylated salt gelling agent" means the gelling agent is formed by the reaction of a salt with a compound containing at least one carboxylic acid group. Preferably the carboxylic acid-containing compound is a fatty acid and the carboxylated salt gelling agent is the salt of a water insoluble fatty acid and a base. While the fatty acid used to make the carboxylated salt gelling agent is generally water insoluble, the resulting gelling agent may be water soluble or water insoluble. Preferably, the carboxylated salt gelling agent in accordance with this invention is water soluble, i.e. after the water insoluble fatty acid is reacted with the metallic cation (such as sodium) the gelling agent is water soluble. Suitable fatty acids used to make the gelling agent are $C_{12-40}$ straight or branched chain, saturated or unsaturated fatty acids. Suitable fatty acids include lauric, myristic, palmitic, stearic, oleic, linoleic, linolenic, behenic, caprylic, stearic, and so on. In addition, oils containing fatty acid mixtures, such as palm kernel, olive, tallow, peanut, rapeseed, and the like may be used as the fatty acid component. Preferred are $C_{16-22}$ fatty acids such as lauric, stearic, or behenic. Most preferred is where the fatty acid is stearic acid.

A variety of cations may be used. Generally the type of cation selected will determine whether the resulting gelling agent is water soluble or water insoluble. Generally cations such as sodium, potassium, or low molecular weight amines or alkanolamines will provide water soluble gelling agents. Suitable amines are ammonia and derivatives thereof Suitable alkanolamines include mono- di- and triethanolamines.

Examples of gelling agents which may be used in the compositions of the invention are sodium, potassium, aluminum, magnesium, or calcium salts of stearic, behenic, caprylic, tallowic, tallic, cocoic, or lauric acids, and so on. Preferably the gelling agent used in the compositions of the invention are water soluble salts of fatty acids and sodium, and in particular sodium stearate.

Polysaccharides are also suitable secondary gelling agents. Examples of polysaccharides include galactans, galactomannans, glucomannans, polyuronic acids, and the like. Preferably the polysaccharides exhibit pendant hydrophilic groups, which are preferably sulfate. Suitable galactans are agar, agarose, kappa carageenan, iota carageenan, lambda carageenan, and the like. Examples of suitable galactomannans are locust bean gum and guar; examples of glucans are cellulose, starch, dextrans, pullulan, beta 1,3- glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on. Also suitable are dextran sulfate, heparin, pectin, sodium alginate, cellulose gum, cellulose acetate priopionate carboxylate, hydroxyethyl cellulose, hydroxypropyl cellulose, and the like. The polysaccharides may be derivatized with various groups such as sulfate, carboxylate, hydroxyl, and so on.

Also suitable for use as the gelling agent are PPC's formed by the reaction of the anionic polysaccharides mentioned above and a protein. The term "protein" when used in accordance with this invention means a peptide chain having at least two amino acid residues, preferably at least five, and more preferably more than one hundred amino acid residues. Most preferably the protein is a high molecular weight polypeptide which is preferably water soluble, and may be natural, plant (vegetable) proteins, or animal derived proteins, as well as synthetic proteins provided they react with the hydrophilic pendant groups on the polysaccharide to form a PPC. The isoelectric point of the protein used to make the PPC is not critical. Examples of natural proteins include albumen, amylase, amyloglucosidase, arginine/ lysine polypeptide, casein, catalase, collagen, crystalline, cytochrome C, deoxyribonuclease, elastin, fibronectin, gelatin, gliadin, glucose oxidase, glycoproteins, hexyldecyl ester of hydrolyzed collagen, human placental protein, human placental enzymes, iodized corn protein, keratin, lactoferrin, lactoglobulin, lactoperoxidase, lipase, milk protein, hyristoyl glycine/histidine/lysin polypeptide, nisin, oxido reductase, pancreatin, papin, pepsin, placental protein, protease, saccharomyces polypeptides, serum albumin, serum protein, silk, sodium stearoyl lactalbumin, soluble proteoglycan, soybean palmitate, soy, egg, peanut, cottonseed, sunflower, pea, whey, fish, seafood, subtilisin, superoxide dismutase, sutilains, sweet almond protein, urease, wheat germ protein, wheat protein, whey protein, zein, hydrolyzed vegetable protein, and the like. Preferred is casein which is a mixture of phosphoproteins obtained from cow's milk; and milk protein which is a mixture of proteins obtained from cow's milk.

Also suitable as gelling agents are anionic polymers, such as acrylic polymers which are generally sold in the form of aqueous solutions or dispersions. Such acrylic polymers may be homo- or copolymers of monomers such as acrylamide, methacrylamide, acrylic acid, methacrylic acid, $C_{1-22}$ alkyl acrylates, $C_{1-22}$ alkyl methacrylates, and so on. The monomers may also be copolymerized with other organic compounds such as alkoxylated fatty alcohols. The resulting polymers may also be cross-linked with cross-linking agents such as the allyl ether of sucrose, pentaerythritol, or propylene. Preferred are copolymers of monomers A or B, wherein A is selected from the group consisting of acrylic acid, methacrylic acid, and mixtures thereof, and B is selected from the group consisting of a $C_{1-22}$ alkyl acrylate, a $C_{1-22}$ alky methacrylate, and mixtures thereof Preferably, the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. The composition of the acrylic copolymer may contain from about 0.1–99 parts of the A monomer, and about 0.1–99 parts of the B monomer. One example of such an acrylic polymer solution is sold by Seppic, Inc., under the tradename Capigel, in particular, Capigel 98, which is a white liquid having a pH of 2 to 4, a solids content of about 29–31, a density of 1.04 to 1.08, and a viscosity of 700–1000 millipascal seconds at 25° C.

Other types of polymers may contain A and B monomers which are copolymerized with alkoxylated fatty alcohols having the general formula:

$$R-(CH_2CH_2O)_nH$$

wherein n is 1–500.

Examples of polymers containing A and B monomers polymerized with alkoxylated alcohols include acrylates/steareth-50 acrylate copolymer, acrylates/steareth-20 methacrylate copolymer, and the like. Such polymers are sold under the tradenames Acrysol and Acculyn by Rohm & Haas, and Antil by Goldschmidt.

Also suitable are homo- or copolymers of monomers A and B above, which are cross-linked with various cross-linking agents such as the allyl ether of sucrose, the allyl ether of pentaerythritol, or the allyl ether of propylene. Examples of these polymers include those sold under the CTFA name Carbomer, which is defined as a homopolymer of acrylic acid crosslinked with an allyl ether of sucrose, pentaerythritol, or propylene. Carbomers are sold under the tradename Carbopol by B. F. Goodrich or Tego by Goldschmidt, as well as other vendors.

Particularly preferred as a secondary gelling agent in the claimed compositions is propylene carbonate.

The invention will be further described in connection with the following examples which are set forth for the purposes of illustration only.

EXAMPLE 1

Nail enamel remover compositions were made according to the following formulas:

|  | w/w % | | | | | |
| --- | --- | --- | --- | --- | --- | --- |
|  | 1 | 2 | 3 | 4 | 5 | 6 |
| Acetone | 45.0 | — | 60.0 | 60.0 | 60.0 | 60.0 |
| Methylgluceth-2 | 3.0 | — | 1.0 | 1.0 | 1.0 | 1.0 |
| Water | 50.0 | 48.0 | 38.45 | 37.45 | 38.17 | 38.285 |
| Laponite XLG | 2.0 | 2.0 | 0.50 | 1.00 | 0.75 | 0.65 |
| Propylene carbonate | — | — | 0.05 | 0.10 | 0.08 | 0.065 |
| Methoxypropanol | — | 50.0 | — | — | — | — |

The compositions were made by combining the water and Laponite and mixing well on a paint shaker for 20 minutes. When the Laponite was dispersed, the methylgluceth-2 and propylene carbonate were added to the composition and it was mixed well for 5 minutes. The organic solvents were added and mixed well for an additional 10 minutes. The compositions were poured into glass containers.

The viscosities of formulas 5 and 6 were measured in centipoise as follows:

| Formula | 15 minute setup viscosity at 20° C. | 24 hour undisturbed viscosity at 20° C. | 24 hour disturbed viscosity at 20° C. |
| --- | --- | --- | --- |
| 5 | 200 | 300 | 120 |
| 6 | 180 | 200 | 40 |

The above results illustrate that the metal silicate gelling agent gels compositions 5 and 6 to a desirable viscosity for nail enamel remover. The disturbed viscosity is substantially less, indicating that when the composition is shaken the viscosity is substantially reduced, but when the solution is allowed to settle the viscosity increases as the gel reforms.

We claim:

1. An aqueous organic solvent based cosmetic remover composition gelled to a viscosity of 25 to 500,000 centipoise with a synthetic metal silicate gelling agent wherein the organic solvent is selected from the group consisting of ketones, esters of organic alcohols, ethers, paraffinic hydrocarbons, and mixtures thereof, wherein the undisturbed viscosity of the composition is greater than the disturbed viscosity.

2. The composition of claim 1 which comprises 1–95% by weight of the total composition of organic solvent.

3. The composition of claim 1 which comprises 0.5–99% by weight of the total composition of water.

4. The composition of claim 1 wherein the metal silicate is a synthetic metal silicate where the metal is sodium.

5. The composition of claim 1 wherein the undisturbed viscosity of the composition is 10 to 90 percent greater than the disturbed viscosity.

6. The composition of claim 1 wherein the organic solvent is volatile.

7. The composition of claim 6 wherein the organic solvent has a vapor pressure of at least 2 mm. of mercury at 20° C.

8. The composition of claim 6 wherein the organic solvent is a paraffinic hydrocarbon, a ketone, or mixtures thereof.

9. The composition of claim 8 wherein the organic solvent is a ketone.

10. The compositon of claim 9 wherein the organic solvent is acetone.

11. The composition of claim 1 wherein the metal silicate is an alkali metal silicate, an alkaline earth metal silicate, or mixtures thereof.

12. The composition of claim 11 wherein the metal is selected from the group consisting of sodium, magnesium, potassium, lithium, and mixtures thereof.

13. The composition of claim 12 wherein the metal silicate has the general formula:

$$[Si_8(Mg_aLi_bH_c)O_{20}(OH)_{4-y}F_y]^{z-}zM+$$

wherein:

a is 4.95 to 5.7 b is from 0 to 1.05 c is from 0 to <2 a+b+c is from >4 to<8 y is from 0 to <4 z=12−2a−b−c

M is Na+ or Li.

14. The composition of claim 1 further comprising 0.001–20% by weight of the total composition of a secondary gelling agent.

15. The composition of claim 14 wherein the secondary gelling agent is selected from the group consisting of acrylic polymers, carboxylated salts, propylene carbonate, and mixtures thereof.

16. The composition of claim 15 wherein the secondary gelling agent is propylene carbonate.

17. The composition of claim 1 further comprising 0.1–20% by weight of the total composition of a surfactant.

18. The composition of claim 17 wherein the surfactant is nonionic.

19. The composition of claim 18 wherein the nonionic surfactant is a polyethylene glycol ether.

20. The composition of claim 19 wherein the nonionic surfactant is methylgluceth-2.

* * * * *